(12) United States Patent
George et al.

(10) Patent No.: US 10,070,955 B2
(45) Date of Patent: Sep. 11, 2018

(54) PROSTHESIS WITH BENDABLE CENTRAL REGION

(75) Inventors: Stephanie A. George, St. Louis Park, MN (US); Sara Elizabeth Nelson, Plymouth, MN (US); Randall P. Rowland, Eden Prairie, MN (US); Charles C. Kuyava, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 602 days.

(21) Appl. No.: 12/272,093

(22) Filed: Nov. 17, 2008

(65) Prior Publication Data

US 2009/0132044 A1    May 21, 2009

Related U.S. Application Data

(60) Provisional application No. 60/988,298, filed on Nov. 15, 2007.

(51) Int. Cl.
*A61F 2/26* (2006.01)

(52) U.S. Cl.
CPC ...................................... *A61F 2/26* (2013.01)

(58) Field of Classification Search
CPC .............................. A61F 2/26; A61F 2002/047
USPC ....................... 623/11.11; 600/38, 39, 40, 41
See application file for complete search history.

(56) References Cited

U.S. PATENT DOCUMENTS

| | | | |
|---|---|---|---|
| 3,832,996 A | 9/1974 | Kalnberz | |
| 3,893,456 A | 7/1975 | Small et al. | |
| 3,987,789 A | 10/1976 | Timm et al. | |
| 3,991,752 A | 11/1976 | Gerow | |
| 4,066,073 A | 1/1978 | Finney et al. | |
| 4,151,840 A | 5/1979 | Barrington | |
| 4,177,805 A | 12/1979 | Tudoriu | |
| 4,187,839 A | 2/1980 | Nuwayser et al. | |
| 4,204,530 A | 5/1980 | Finney | |
| 4,244,370 A | 1/1981 | Furlow et al. | |
| 4,345,339 A | 8/1982 | Muller et al. | |
| 4,353,360 A | 10/1982 | Finney et al. | |
| 4,392,562 A * | 7/1983 | Burton .................... | A61F 2/26 600/40 |
| 4,411,260 A | 10/1983 | Koss | |
| 4,411,261 A | 10/1983 | Finney | |
| 4,483,331 A | 11/1984 | Trick | |
| 4,517,967 A | 5/1985 | Timm et al. | |
| 4,522,198 A | 6/1985 | Timm et al. | |

(Continued)

FOREIGN PATENT DOCUMENTS

| EP | 0137752 B1 | 8/1989 |
|---|---|---|
| EP | 0774935 B1 | 7/1995 |

(Continued)

OTHER PUBLICATIONS

Acu-Form Penile Prosthesis, Mentor, 1 page Aug. 1997.

(Continued)

*Primary Examiner* — Leslie Lopez
(74) *Attorney, Agent, or Firm* — Brake Hughes Bellermann LLP

(57) ABSTRACT

A prosthetic device including a column of resilient material that has a central region between the proximal and distal ends. The central region has a reduced diameter relative to the proximal and distal ends. Discs protrude from the central region.

16 Claims, 1 Drawing Sheet

(56) References Cited

U.S. PATENT DOCUMENTS

| | | | |
|---|---|---|---|
| 4,541,420 | A | 9/1985 | Timm et al. |
| 4,545,081 | A | 10/1985 | Nestor et al. |
| 4,594,998 | A | 6/1986 | Porter et al. |
| 4,619,251 | A | 10/1986 | Helms et al. |
| 4,665,902 | A | 5/1987 | Goff et al. |
| 4,666,428 | A | 5/1987 | Mattioli et al. |
| 4,669,456 | A | 6/1987 | Masters |
| 4,693,719 | A | 9/1987 | Franko et al. |
| 4,699,128 | A | 10/1987 | Hemmeter |
| 4,807,608 | A | 2/1989 | Levius |
| 4,881,531 | A | 11/1989 | Timm et al. |
| 4,899,737 | A | 2/1990 | Lazarian |
| 4,988,357 | A | 1/1991 | Koss |
| 5,050,592 | A | 9/1991 | Olmedo |
| 5,067,485 | A * | 11/1991 | Cowen ........................... 600/40 |
| 5,167,611 | A * | 12/1992 | Cowan ........................... 600/40 |
| 5,176,708 | A | 1/1993 | Frey et al. |
| 5,283,390 | A | 2/1994 | Hubis et al. |
| 5,445,594 | A | 8/1995 | Elist |
| 5,468,213 | A * | 11/1995 | Polyak ..................... A61F 2/26 600/40 |
| 5,509,891 | A | 4/1996 | DeRidder |
| 5,512,033 | A * | 4/1996 | Westrum et al. ............... 600/40 |
| 5,553,379 | A | 9/1996 | Westrum, Jr. et al. |
| 6,579,230 | B2 | 6/2003 | Yachia et al. |
| 6,600,108 | B1 | 7/2003 | Mydur et al. |
| 2004/0193283 | A1* | 9/2004 | Rioux ................... A61M 25/04 623/23.66 |
| 2005/0014993 | A1 | 1/2005 | Mische |
| 2008/0103353 | A1 | 5/2008 | Jahns et al. |

FOREIGN PATENT DOCUMENTS

| | | |
|---|---|---|
| GB | 2151484 A | 7/1985 |
| WO | WO8601398 A1 | 3/1986 |
| WO | WO9604865 A1 | 2/1996 |

OTHER PUBLICATIONS

Agrawal, Wineet, et al., An Audit of Implanted Penile Prostheses in the UK, BJU International pp. 393-395 (2006).

Akand, Murat Mechanical Failure With Malleable Penile Prosthesis, J. Urol. 70: 1007.e11-1007.e12 (2007).

AMS Malleable 600.TM. American Medical Systems Publication 30915, 1983.

Anafarta, Kadri, Clinical Experience With Inflatable and Malleable Penile Implants in 104 Patients, Urol. Int. 56: 100-104 (1996).

Benson RC Jr, Patterson DE, Barrett DM. Long-term results with the Jonas malleable penile prosthesis. J Urol. Nov. 1985;134(5):899-901.

Burns-Cox, N., Fifteen Years Experience of Penile Prosthesis Insertion, International J. Impotence Res. (1997) 9, 211-216.

Chiang, Han-Sun, 10 Years of Experience With Penile Prosthesis Implantation in Taiwanese Patients, J. Urol. vol. 163: 476-480 (2000).

Choi, Hyung Ki, Ten Years of Experience With Various Penile Prosthesis in Korean, Yasel Medical J. Wol. 35, No. 2, (1994) 209-217.

Dorfinger T, Bruskewitz R. AMS malleable penile prosthesis. Urology. Dec. 1986;28(6):480-5.

Durazi, Mohammed et al., Penile Prosthesis Implantation for Treatment of Postpriapism Erectile Dysfunction, Urol. J. 2008:5:115-9.

Fathey, Ahmad, Experience With Tube (PROMEDON_ Malleable Penile Implant, Urol. Int. 2007; 79:244-247.

Ferguson, Kenneth, Prospective Long-Term Results and Quality-Of-Life- Assessment After Dura-II Penile Prosthesis Placement, Urol. 61(2) 437-441 (2003).

Fogarty, JD, Cutaneous Temperature Measurements in Men With Penile Prostheses: A Comparison Study, Int. J. of Impotence Res. (2005) 17, 506-509.

Henry, Gerard D., Advances in Penile Prosthesis Design, Curr Sex Health report 2007;4:15-19.

Jonas U. [Silicone-silver penis prosthesis (Jonas-Eska), long-term reconstruction. J Urol. Sep. 1998;160(3 Pt 2):1164-8.

Kardar, A.H., An Unusual Complication of Penile Prosthesis Following Urethroplasty, Scand. J. Urol. Nephrol. 36: 89-90, 2002.

Kaufman JJ, Raz S. Use of implantable prostheses for the treatment of urinary incontinence and impotence. Am J Surg. Aug. 1975;130(2):244-50.

Khoudary, Kevin, Design Considerations in Penile Prostheses: The American Medical Systems Product Line, J. Long-Term Effects of Medical Implants, 7(1):55-64 (1997).

Kimoto, Yasusuke et al., JSSM Guidleines for Erectile Dysfunction, Int. J. Urol (2008) 15, 564-76.

Krauss, Dennis J., Use of the Malleable Penile Prosthesis in the Treatment of Erectile Dysfunction: A Prospective Study of Postoperative Adjustment, J. Urol. vol. 142: 988-991 (1989).

Lazarou, Stephen, Technical Advances in Penile Prostheses, J. Long-Term effects of Medical Implants, 16(3):235-247 (2006J.

Leriche, Albert, et al., Long-Term Outcome of Forearm Flee-Flap Phalloplasty in the Treatment of Transexualism, BJU Int. (2008) 101, 1297-1300.

Maul Judd, Experience With the AMS 600 Malleable Penile Prosthesis, J Urol. 135:929-931 (1986).

Mentor Urology Products, 18 pages (May 1998).

Merino, G. Atienza, Penile Prosthesis for the Treatment of Erectile Dysfunction, Actas Urol. Esp. 2006: 30 (2): 159-169.

Minervini, Andrea, Outcome of Penile Prosthesis Implantation for Treating Erectile Dysfunction: Experience With 504 Procedures, BJU International 97:129-133, (2005).

Montague, Drogo, Clinical Guidelines Panel on Erectile Dysfunction: Summary Report on the Treatment of Organic Erectile Dysfunction, J. Urol. 156:2007-2011 (1996).

Montague, Drogo, Contemporary Aspects of Penile Prosthesis Implantation, urol Int. 2003: 70: 141-146.

Montague, Drogo, Current Status of Penile Prosthesis Implantation, Urology Reports 2000, 1: 291-296.

Montague, Drogo, Experience With Semirigid Rod and Inflatable Penile Prostheses, J. Urol. 129:967-968, 1983.

Montague, Drogo, Penile Prosthesis Implantation for End-Stage Erectile Dysfunction After Radical Prostatectomy, Reviews in Urol. vol. 7 Suppl. 2 S51-S57 2005.

Montague, Drogo, Penile Prosthesis Implantation, 712-719 1994.

Montague, Drogo, Surgical Approaches for Penile Prostheses Implantation: Penoscrotal Vs Infrapubic, International J. Impotence Res. (2003) 15, Suppl. 5 , S134-S135.

Morey, Allen, et al, Immediate Insertion of a Semirigid Penile Prosthesis For Refractory Ischemic Priapism, Military Medicine, 172, 11:1211, 2007.

Mulcahy, John, Another Look at the Role of Penile Prostheses in the Management of Impotence, Urology Annual 11, pp. 169-185 (1997).

Natali, Alessandro, et al., Penile Implantation in Europe: Successes and Complications With W53 Implants in Italy and Germany, J Sex. Med. 2008;5:1503-12.

Paula, B. G. Revision Surgery for Penile Implants, Int. J. Impotence res. (1994) 6, 17-23.

Pearman RO. Insertion of a silastic penile prosthesis for the treatment of organic sexual impotence. J Urol. May 1972;107(5):802-6.

Randrup, Eduardo, Penile Implant Surgery: Rear Tip Extender That Stays Behind, Urology 1992 34,1 p. 87.

Rhee, Eugene, Technique for Concomitant Implantation of the Penile Prosthesis With the Male Sling, J. Urol. 173: 925-927 (2006).

Salama, Nadar, Satisfaction With the Malleable Penile Prosthesis Among Couples From the Middle East: Is It Different From That Reported Elsewhere?, Int. J. Impotence Res. 16:175-180 (2004).

Simmons, M, et al., Penile Prosthesis Implantation: Past, Present and Future, Int. J. Impotence Res. (2008) 20, 437-44.

Small, Michael, Small-Carrion Penile Prosthesis: A Report on 160 Cases and Review of the Literature, J. Urol. vol. 167, 2357-2360, Jun. 2002.

(56) References Cited

OTHER PUBLICATIONS

Smith, Christopher, Management of Impending Penile Prosthesis Erosion With a Polytetrafluoroethylene Distal Wind Sock Graft, J. Urol. vol. 160: 2037-2040, (1998).
Stein, Avi et al., Malleable Penile Prosthesis Removal Leaving Behind the Rear Tip Extenders: A Clinical Presentation, Urol. Int. 50:119-120 (1993).
Surgical Protocol, Mentor 5 pages Sep. 1997.
The AMS Hydroflex Self-Contained Penile Prosthesis, American Medical Systems Publication 50513 (1985).
Yoo JJ, Lee I, Atala A. Cartilage rods as a potential material for penile reconstruction. J Urol. Sep. 1998;160(3 Pt 2):1164-8; discussion 1178.
Zerman, Dirk-Henrik, et al. Penile Prosthetic Surgery in Neurologically Impaired Patients: Long-Term Follow-Up, J Urol 175: 1041-1044. (2006).

* cited by examiner

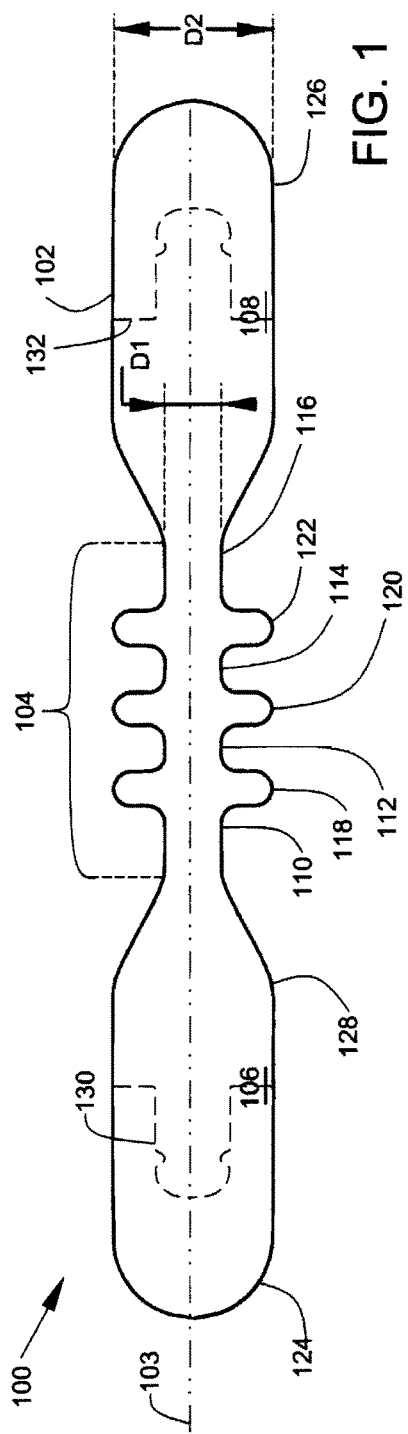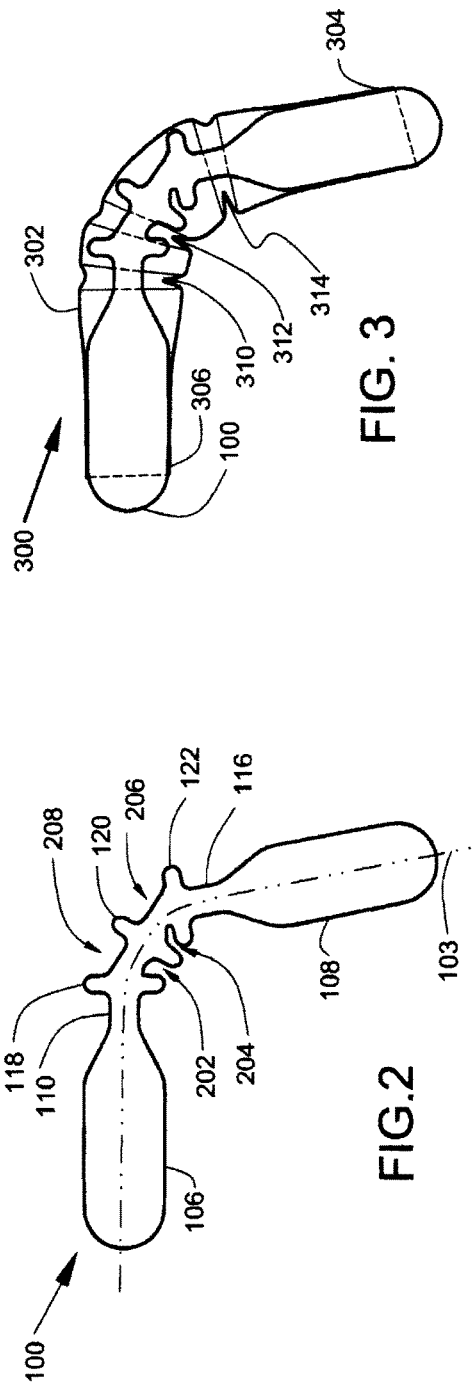

PROSTHESIS WITH BENDABLE CENTRAL REGION

CLAIM TO PRIORITY

The present application claimed priority to U.S. Provisional Patent Application No. 60/988,298, filed Nov. 15, 2007, and entitled "Prosthesis with Bendable Central Region." The identified provisional patent application is hereby incorporated by reference in its entirety.

FIELD OF THE INVENTION

The present invention relates to implantable prostheses. In particular, but not by way of limitation, the present invention relates to implantable malleable (non-inflatable) penile prostheses.

SUMMARY OF THE INVENTION

Disclosed is a prosthetic device. The prosthetic device comprises a column. The column comprises resilient material. The column comprises a central region between the proximal and distal ends. The central region has a reduced diameter relative to the proximal and distal ends. Discs protrude from the central region.

BRIEF DESCRIPTION OF THE DRAWINGS

FIG. 1 illustrates a prosthetic device in a straight position
FIG. 2 illustrates a prosthetic device in a bent position.
FIG. 3 illustrates a prosthetic device that includes a sheath.

DETAILED DESCRIPTION OF ILLUSTRATIVE EMBODIMENTS

FIG. 1 illustrates a prosthetic device 100. The prosthetic device 100 comprises a column 102 formed of resilient material. The column 102 comprises an annular shape that is generally symmetric about a lengthwise axis 103. In one embodiment, the column 102 encloses an internal malleable core or other known type of penile prosthesis core. In another embodiment, the column 102 does not include a core. The column 102 comprises a central region 104 between a proximal end 106 and a distal end 108. The central region 104 includes one or more annular groove regions 110, 112, 114, 116 that have a diameter D1 that is reduced relative to a diameter D2 of the proximal and distal ends 106, 108. The reduced diameter annular groove regions 110, 112, 114, 116 are spaced apart from one another by intervening discs 118, 120, 122 that have a larger diameter than the reduced diameter D1.

In one embodiment, the column 102 is formed as a single unitary, seamless component that is molded, cast, or machined to final shape. This unitary manufacturing method is economical. In another embodiment, the column 102 is formed of end caps (tip extenders) 124, 126 that join a central body 128 along joint lines 130, 132. The joint lines 130, 132 are annular and form a snap attachment profile between the column and the end caps 124, 126. The use of end caps 124, 126 of different lengths and shapes allows the prosthetic device 100 to be conveniently sized by a physician to vary the cylinder length while maintaining a central body 128 that is common to the different sizes and shapes. Alternatively, the central body 128 and a first end cap 124 can formed as a seamless unitary body, and a second end cap 126 can have different lengths and shapes. In this alternative embodiment, rear tip extenders (RTEs) can be used as the second end caps 126.

As illustrated in FIG. 1, the prosthesis 100 is in a generally straight alignment. The discs 118, 120, 122 extend outwardly as illustrated to provide closely spaced annular protrusions that function to maintain girth along the central region 104.

FIG. 2 illustrates the prosthesis 100 in a bent position. The prosthesis is bent through an angle as illustrated. The annular groove regions 110, 112, 114, 116 require less force to bend because of their small diameter D1. When the prosthesis is bent, stress tends to concentrate at the smaller diameter zones. Bending takes place predominantly in the annular groove regions because of their smaller diameter D1.

Bending tends to compress resilient material on the inside of a bend, and the compressed material tends to exert a springback force. The term "springback" refers to the amount of a return movement of a bent column after a bending force is removed. Springback causes a column that is bent into a position (either a straight or bent position) to lose part of the bend after the column is released. Springback is an undesirable property that adversely affects concealability. Springback requires the user to learn to bend the column past a desired position in order for it to have the desired position after springback, or requires the user to bend the column multiple times in order to obtain a concealed position. As illustrated, on the inside of the bend at locations 202, 204, annular grooves have eliminated material which would otherwise be compressed. The grooves at locations 202, 204 reduce springback due to avoiding compression of material.

Bending tends to stretch (place in tension) resilient material on the outside of the bend, and the stretched material tends to exert a springback force. As illustrated, on the outside of the bend at locations 206, 208, annular grooves have eliminated material which would otherwise be stretched. The grooves at locations 206, 208 reduce springback due to avoiding stretching of material.

The material remaining inside the grooves (such as grooves 112, 114), in other words the material within diameter D1 is close to a main cylinder axis (along a bent central axis 103) for bending where both compression and stretching tends to be reduced. There is thus little contribution to springback from the material within diameter D1.

The grooves have a combination of width and depth (groove aspect ratio) that provides a desirable wide bending angle at each groove before adjacent disc edges bend far enough to contact one another.

The prosthesis 100 has overall desirable large girth characteristics associated with the larger diameter D2 and the multiple discs 118, 120, 122, in combination with the desirable small springback characteristics associated with the smaller diameter D1. The desired large girth characteristics are maintained through the region 104 by the presence of the discs 118, 120, 122.

FIG. 3 illustrates an embodiment of a prosthesis 300. The prosthesis 300 comprises a column 100 as described above in connection with FIGS. 1-2. The prosthesis 300 comprises a flexible sheath 302 that surrounds a substantial portion of the length of the column 100 as illustrated. The flexible sheath 302 has ends 304, 306 that are attached to the column 100. A central portion of the flexible sheath 302 includes annular corrugations 310, 312, 314 that slide easily along the length of the column 100 so that bending the sheath does not build up any substantial internal stretching or compressive forces in the sheath 302 that could otherwise contribute to undesired springback. The sheath 302 can comprise materials such as silicone, urethane or polyurethane and other known flexible biocompatible materials. The sheath 302 tends to span across and cover up grooves (such as grooves 110, 112, 114, 116), giving the assembled prosthesis 300 a desired overall isodiametric shape, sensation and appearance. Sheaths 302 can be provided in different wall thickness to provide different girths adapted to individual patients, reducing inventory requirements for girth sizes of columns 100.

The semi-rigid rod types of penile prosthesis disclosed offer a patient a device with good column strength and rigidity. The ability to conceal the device by positioning these rods in a bent configuration and remaining in that concealed position is provided.

The internal core structure can comprise wires and/or fabric and/or plastic components (interlocking rings.) The two ends can have profiles 130 that would accept snap attachment rear tip extenders, for finer length dimensioning to better fit the patient's anatomy.

The addition of discs (hubs or rings) along a smaller diameter center section allows the rod to maintain a more concealed position for the patient. The discs (hubs or rings), with or without an outer sheath, would give the rod an outward appearance and sensation of being an isodiametric rod. Existing internal rod components (AMS 600, AMS 600M, AMS 650, DURA II) and rear tip extenders (AMS 700 IPP or AMS Ambicor) can be adapted for use in the embodiments. The prosthesis can have a sheath or "skin" that would give the appearance of the rod being isodiametric. The ends of the rods could have snap attachment profiles to accept the existing AMS 700 RTEs. Inside cores from the AMS 600, AMS 600M, AMS 650, DURA II can be adapted for use.

Although the present invention has been described with reference to preferred embodiments, workers skilled in the art will recognize that changes may be made in form and detail without departing from the spirit and scope of the invention.

What is claimed is:

1. A malleable, non-inflatable penile prosthetic device, comprising:
   a column enclosing an internal malleable core, the column being a unitary and continuous body having a proximal end portion, a distal end portion, and a central region, the distal end portion having a first rounded portion at a distal-most end of the column, a first constant diameter portion having a first constant diameter, and a first tapered portion that tapers to the central region, the first constant diameter extending between the distal-most end and the first tapered portion, the first rounded portion crossing a central axis of the column when the column is a linear configuration, the proximal end portion having a second rounded portion at a proximal-most end of the column, a second constant diameter portion having a second constant diameter, and a second tapered portion that tapers to the central region, the second constant diameter extending between the proximal-most end and the second tapered portion, the central region being disposed between the proximal end portion and the distal end portion, the central region having a reduced diameter that is less than the first constant diameter of the distal end portion and the second constant diameter of the proximal end portion;
   discs protruding from the central region, wherein the discs maintain a constant girth that is larger than the reduced diameter; and
   a sheath covering the column and the discs and extending between the distal end portion and the proximal end portion.

2. The prosthetic device of claim 1, wherein the discs are attached to the central region.

3. The prosthetic device of claim 1, wherein a first end of the sheath is attached to the first constant diameter portion of the distal end portion, and a second end of the sheath is attached to the second constant diameter portion of the proximal end portion.

4. The prosthetic device of claim 1, wherein each of the distal end portion and the proximal end portion is devoid of any of the discs.

5. The prosthetic device of claim 1, wherein the sheath comprises annular corrugations.

6. The prosthetic device of claim 1, wherein the discs are spaced apart from one another along a longitudinal axis of the central region, the discs having a diameter that is greater than the reduced diameter.

7. The prosthetic device of claim 1, wherein the column is formed of a resilient material, the column having an annular shape that is symmetric about a lengthwise axis of the column.

8. The prosthetic device of claim 1, wherein the first constant diameter portion of the distal end portion has a length that is a majority of a length of the distal end portion, and the second constant diameter portion of the proximal end portion has a length that is a majority of a length of the proximal end portion.

9. The prosthetic device of claim 1, wherein the column has a longitudinal axis extending along a length of the column, the column having a central axis, perpendicular to the longitudinal axis, that divides the column into a first part and a second part, the second part being symmetrical to the first part.

10. A prosthetic device, comprising:
    a unitary body enclosing an internal malleable core, the unitary body having a proximal end portion, a distal end portion, and a central region, the distal end portion having a first rounded portion at a distal-most end of the unitary body, a first constant diameter portion having a first constant diameter, and a first tapered portion that tapers to the central region, the first constant diameter extending between the distal-most end and the first tapered portion, the first rounded portion crossing a central axis of the unitary body when the unitary body is a linear configuration, the proximal end portion having a second rounded portion at a proximal-most end of the column, a second constant diameter portion having a second constant diameter, and a second tapered portion that tapers to the central region, the second constant diameter extending between the proximal-most end and the second tapered portion,
    the central region of the unitary body defining a plurality of annular grooves having a reduced diameter that is less than the second constant diameter of the proximal end portion and the first constant diameter of the distal end portion, the plurality of annular grooves being spaced apart from each other by intervening discs having a diameter larger than the reduced diameter, wherein the plurality of annular grooves are openings between the intervening discs and the unitary body is devoid of material between the intervening discs; and a sheath having a first end portion coupled to the proximal end portion of the unitary body and a second end portion coupled to the distal end portion of the unitary body.

11. The prosthetic device of claim 10, wherein the sheath includes a central portion disposed between the first end portion of the sheath and the second end portion of the sheath, the central portion of the sheath being configured to move with respect to the unitary body.

12. The prosthetic device of claim 10, wherein the sheath includes a central portion disposed between the first end portion of the sheath and the second end portion of the sheath, the central portion of the sheath being configured to move with respect to the unitary body, the central portion of the sheath defining annular corrugations.

13. The prosthetic device of claim 10, wherein the first constant diameter is the same as the second constant diameter.

14. The prosthetic device of claim 10, wherein the sheath is flexible.

15. The prosthetic device of claim 10, wherein the unitary body is formed of a resilient material, the unitary body having an annular shape that is symmetric about a lengthwise axis of the unitary body.

16. The prosthetic device of claim 10, wherein the proximal end portion and the distal end portion are devoid of any of the annular grooves and any of the intervening discs.

\* \* \* \* \*